United States Patent [19]
Ishida et al.

[11] Patent Number: 5,231,864
[45] Date of Patent: Aug. 3, 1993

[54] AIR-FUEL RATIO DETECTING DEVICE

[75] Inventors: Tetsuro Ishida; Nobuaki Murakami; Yoshiaki Danno, all of Kyoto, Japan

[73] Assignee: Mitsubishi Jidosha Kogyo Kabushiki Kaisha, Tokyo, Japan

[21] Appl. No.: 661,614

[22] Filed: Feb. 28, 1991

[30] Foreign Application Priority Data

Feb. 28, 1990 [JP] Japan .................... 2-48418
Jul. 31, 1990 [JP] Japan .................... 2-204327

[51] Int. Cl.$^5$ ............................. G01N 27/416
[52] U.S. Cl. .................... 73/23.32; 204/406; 436/137
[58] Field of Search ........... 73/23.32; 436/137; 123/489, 492; 204/406

[56] References Cited

U.S. PATENT DOCUMENTS

| | | | |
|---|---|---|---|
| 4,578,172 | 3/1986 | Yamada et al. | 204/412 |
| 4,770,758 | 9/1988 | Suzuki et al. | 204/406 |
| 4,842,711 | 6/1989 | Asakura et al. | 204/406 |
| 4,891,121 | 1/1990 | Hirako et al. | 204/406 |
| 4,891,122 | 1/1990 | Danno et al. | 204/406 |
| 4,908,765 | 3/1990 | Murakami et al. | 123/492 X |
| 4,934,328 | 6/1990 | Ishii et al. | 123/489 |

FOREIGN PATENT DOCUMENTS

| | | | |
|---|---|---|---|
| 0136144 | 3/1985 | European Pat. Off. | |
| 2183042 | 5/1987 | United Kingdom | 436/137 |
| 2193327 | 2/1988 | United Kingdom | |
| 2208007 | 2/1989 | United Kingdom | 73/23.32 |

Primary Examiner—Hezron E. Williams
Assistant Examiner—Joseph W. Roskos

[57] ABSTRACT

An air fuel ratio detecting device is disposed in an exhaust gas passage of an engine, and detects the oxygen concentration in exhaust gases to produce a signal indicative of the air-fuel ratio of an air-fuel mixture supplied to the engine. The air-fuel ratio detecting device serves as a linear A/F sensor for detecting whether the air-fuel mixture is on a leaner or richer side of a stoichiometric ratio and for also detecting the value of the air-fuel ratio. An electric signal representative of the oxygen concentration in a detection chamber supplied with exhaust gases is applied by a sensor cell to a controller which then controls a pump cell to cause the oxygen concentration in the detection chamber to indicate a nearly stoichiometric ratio. The air-fuel ratio detecting device can continuously detect the air-fuel ratio with an electric control signal from the controller. The stoichiometric ratio is detected when the potential difference between the electrode of the pump cell jumps or varies discontinuously. Since the oxygen concentration difference directly serves as detected stoichiometric ratio information, the stoichiometric ratio can be detected with an increased response. The stoichiometric ratio may be detected, using a variable threshold value, based on the potential difference across the pump cell, and the threshold value is selected depending on a control parameter for fine adjustments of a target air-fuel ratio.

18 Claims, 10 Drawing Sheets

AIR-FUEL RATIO DETECTING DEVICE

BACKGROUND OF THE INVENTION

1. Field of the Invention

The present invention relates to an air-fuel ratio detecting device known as a linear A/F (air-fuel ratio)sensor for detecting an air-fuel ratio, and more particularly to an air-fuel ratio detecting device for accurately detecting a stoichiometric air-fuel ratio for an air-fuel mixture to be supplied to a combustion apparatus such as an internal combustion engine.

2. Related Art

There has been proposed a linear A/F sensor utilizing the oxygen concentration cell capability and oxygen ion pumping capability of zirconia, for detecting whether the air-fuel ratio is on a leaner or richer side of a stoichiometric ratio and also for detecting the value of the air-fuel ratio (see Japanese Laid-Open Patent Publication No. 63(1988)-36140).

One conventional linear A/F sensor will be described below with reference to FIGS. 13 through 16 of the accompanying drawings.

Figures 13, 14:
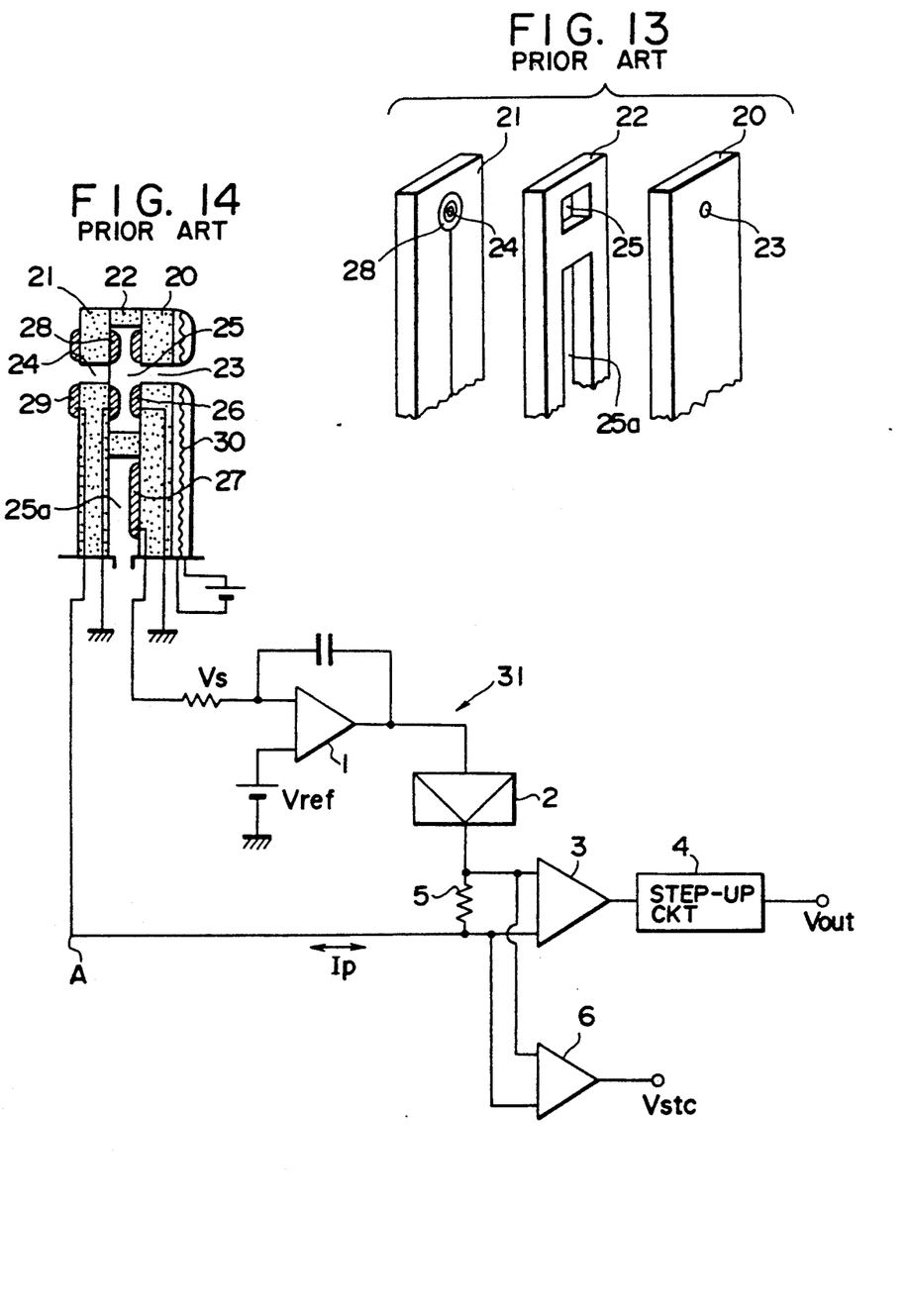
FIG. 13 is an exploded perspective view of a sensor assembly of a conventional air-fuel ratio detecting device.
FIG. 14 is a schematic view, partly in block form, of the conventional air-fuel ratio detecting device shown in FIG. 13.

FIG. 13 shows a linear A/F sensor including a sensor cell 20 and a pump cell 21 which are shown detached from each other, and each include a stabilized zirconia device. The sensor cell 20 and the pump cell 21 are coupled to each other through an insulation layer 22. The sensor cell 20 and the pump cell 21 have respective diffusion holes 23, 24 defined therein for passing therethrough exhaust gases while controlling the speed thereof. The insulation layer 22 has a detecting cavity 25 defined therein into which exhaust gases can be introduced through the diffusion holes 23, 24 by the sensor cell 20 and the pump cell 21. The detecting cavity 25 serves as an element for controlling the speed at which the exhaust gases are diffused. The insulation layer 22 also has a reference chamber 25a positioned below the detecting cavity 25 in spaced-apart relation thereto, the reference chamber 25a being defined between the sensor cell 20 and the pump cell 21. A reference gas such as atmospheric air is introduced into the reference chamber 25a through a communication hole (not shown).

As shown in FIG. 14, the sensor cell 20 has porous electrodes 26, 27 of platinum, and the pump cell 21 has porous electrodes 28, 29 of platinum. The linear A/F sensor also has an electric heater 30 for heating itself to a temperature range, e.g., 800°±100° C., in which the sensor cell 20 and the pump cell 21 can operate without fail.

The sensor cell 20 functions as a conventional $O_2$ sensor for developing an electromotive force, depending on the oxygen concentration difference, between the electrodes 26, 27. The pump cell 21 serves to pump oxygen from a negative electrode to a positive electrode when an electric current (pump current Ip) is caused to flow between the electrodes 28, 29.

Figure 15:
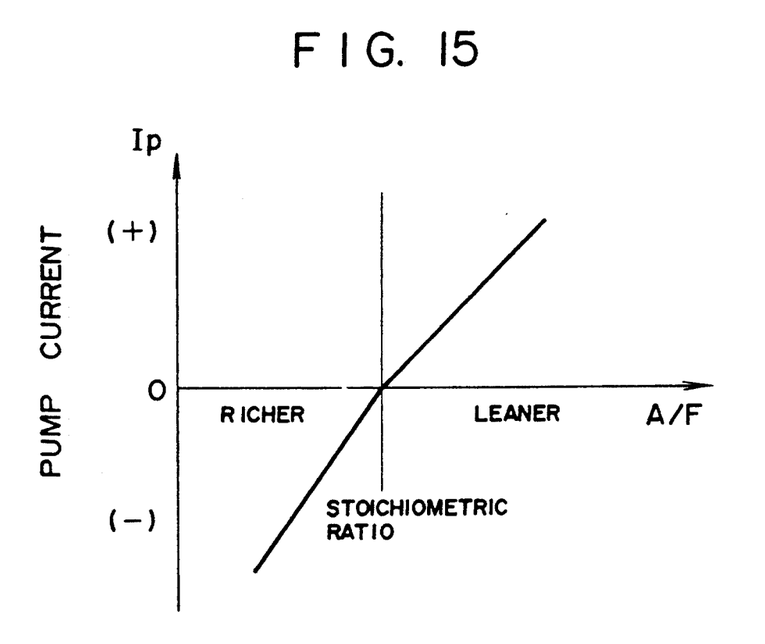
FIG. 15 is a diagram showing the relationship between a pump current and an air-fuel ratio.
Figure 16:
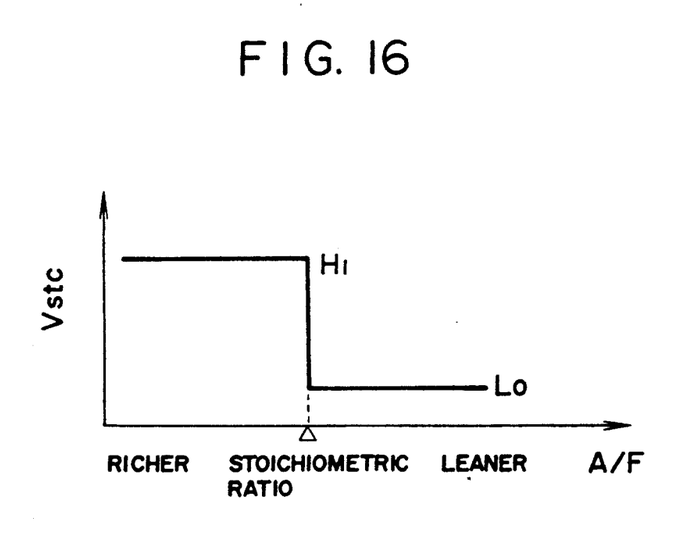
FIG. 16 is a diagram showing a stoichiometric ratio signal with its level depending on the direction of the pump current.

A controller 31 detects an electromotive force Vs developed by the sensor cell 20, and also controls the pump current Ip through a feedback loop to energize the pump cell 21 in order to keep an oxygen concentration corresponding to a stoichiometric ratio in the cavity 25 or the diffusion holes 23, 24. Since the pump current Ip continuously varies with respect to the air-fuel ratio, as shown in FIG. 15, the air-fuel ratio can be calculated from the pump current Ip.

More specifically, the controller 31 includes a comparator 1 and an integrator amplifier 2 with positive and negative power supplies. The comparator 1 compares the electromotive force Vs and a reference voltage Vref corresponding to the stoichiometric ratio. The output signal from the comparator 1 is integrated by the integrator amplifier 2, whose integral output signal is applied as the pump current Ip to the pump cell 21 through a resistor 5.

At this time, a voltage drop across the resistor 5 is detected by a current detector 3 which produces a voltage signal commensurate with the pump current Ip. Therefore, the pump current Ip is detected indirectly by the current detector 3. The output signal of the current detector 3 is applied to a step-up circuit 4 which then produces an output signal Vout, in the range of from 0 to 5 volts, as representing the air-fuel ratio, according to the following equation:

$$V\text{out} = G.Ip + V\text{stp} \tag{1}$$

where G is the current-to-voltage conversion gain of a current-to-voltage converter which is composed of the resistor 5 and the current detector 3, and Vstp is a step-up voltage in the range of from 0 to 5 volts.

With the conventional linear A/F sensor, the air-fuel ratio is detected depending on the pump current Ip which is produced under the feedback control. Therefore, the detected air-fuel ratio is subjected to errors of the feedback control circuit arrangement, such as fluctuation of the reference voltage Vref, an error of the integrator amplifier 2, an error of the step-up circuit 4, or the like. The detected air-fuel ratio is less accurate than a stoichiometric ratio which would be detected solely on the basis of an electromotive force depending on the oxygen concentration difference.

Figure 9:
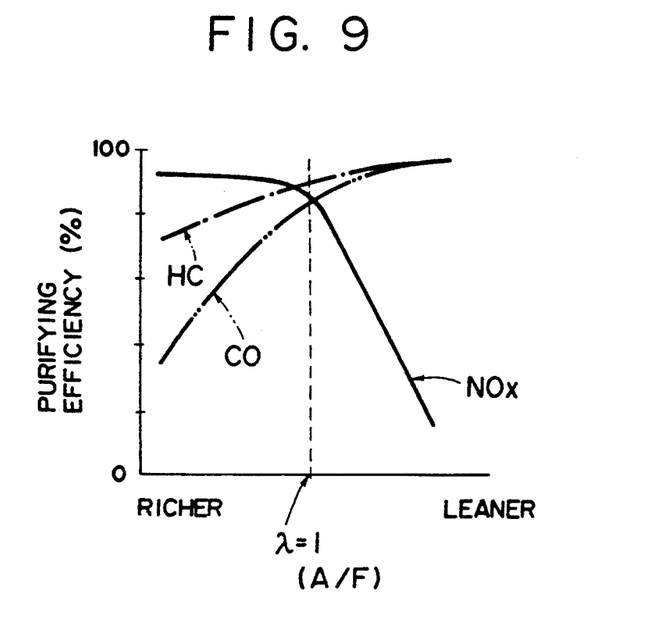
FIG. 9 is a diagram showing purification characteristics of a three-way catalytic converter.

Automotive emission control systems with three-way catalytic converters are required to control the air-fuel ratio within a narrow range or window close to a stoichiometric ratio. Therefore, it is important to detect the stoichiometric ratio with high accuracy because the three-way catalytic converter can achieve a well-balanced purification of toxic pollutants with a high purifying efficiency in the vicinity of the stoichiometric ratio, as shown in FIG. 9.

The conventional linear A/F sensor of the type described above is employed in some automotive emission control systems for purifying exhaust gases with respect to a wide range of air-fuel ratios. Under certain engine operating conditions, such automotive emission control systems are required to effect a stoichiometric ratio feedback control process for keeping the air-fuel ratio within a narrow range or window. If the air-fuel ratio falls out of the window, the three-way catalytic converter would fail to purify the exhaust gases with high efficiency. To avoid such a drawback by minimizing any errors in the feedback control system in the linear A/F sensor shown in FIG. 14, the voltage drop across the resistor 5 is supplied to a current inversion detector 6 to detect the direction in which the pump current Ip flows. A stoichiometric ratio signal Vstc produced by the current inversion detector 6 is thus indicative of the direction of the pump current Ip.

More specifically, as shown in FIG. 15, the pump current Ip is positive when the air-fuel ratio is on the leaner side of the stoichiometric ratio, and negative when the air-fuel ratio is on the richer side of the stoichiometric ratio. The pump current Ip as it is thus inverted is detected by the current inversion detector 6 as the stoichiometric ratio signal Vstc which switches between high and low levels at the stoichiometric ratio. Since the stoichiometric ratio signal Vstc does not contain an error of the gain G and an error of the step-up voltage Vstp, the stoichiometric ratio can be detected with high accuracy.

However, the stoichiometric ratio signal Vstc produced by the current inversion detector 6 still contains other errors of the feedback control system, e.g., an error of the reference voltage Vref and an error of the integrator amplifier 2. Inasmuch as the components of the feedback control system are subject to aging errors, the accuracy with which the stoichiometric ratio is detected remains to be improved. In addition, the pump current Ip based on which the stoichiometric ratio is detected contains a time lag caused by the controller 31, with the result that the stoichiometric ratio feedback control process based on the pump current Ip is relatively slow in response.

Different automobile types are characterized by different proportions and quantities of exhaust gas components at the inlet of the three-way catalytic converter. Furthermore, different catalyst types have slightly different exhaust gas purification characteristics, which results in different air-fuel ratios to achieve high purifying efficiencies of three-way catalytic converters. In view of these problems, there has been a demand for a system for effecting fine adjustments of a target air-fuel ratio in order to control the purifying efficiency of a three-way catalytic converter at a high level.

SUMMARY OF THE INVENTION

It is an object of the present invention to provide an air-fuel ratio detecting device which can detect a stoichiometric ratio with high accuracy to achieve an increased air-fuel ratio control response, and which can also carry out fine adjustments of a target air-fuel ratio.

According to a first aspect of the present invention, there is provided an air-fuel ratio detecting device comprising a sensor, having a first detection surface which defines a detection chamber for introducing an exhaust gas atmosphere produced upon combustion of an air-fuel mixture through a diffusion hole, for generating an electric signal depending on the concentration of oxygen in a gas in the detection chamber, an oxygen ion conduction pump cell, having a second detection chamber surface, which defines the detection chamber, an exhaust gas surface for exposure to the exhaust gas atmosphere, and electrodes mounted respectively on the second detection chamber surface and the exhaust gas surface, for forcibly moving oxygen ions between the second detection chamber surface and the exhaust gas surface in response to an electric control signal applied between the electrodes and for generating an electromotive force depending on the difference between the concentration of oxygen in the gas in the detection chamber and the concentration of oxygen in the exhaust gas atmosphere, control means for applying the electric control signal between the electrodes in order to cause the gas in the detection chamber to indicate a nearly stoichiometric ratio in response to the electric signal from the sensor, first detecting means for producing an air-fuel ratio signal corresponding to the concentration of oxygen in the exhaust gas atmosphere based on the magnitude of the electric control signal, and second detecting means for detecting a voltage between the electrodes and producing a detected output signal when the exhaust gas atmosphere indicates a stoichiometric ratio.

Each of the electrodes is porous and made of platinum. The pump cell is made of zirconia. The oxygen ion conduction pump cell is heated by an electric heater.

The sensor comprises an oxygen ion conduction sensor cell. The sensor cell has a reference chamber surface defining a reference chamber for being filled with a reference gas having an air excess ratio which is sufficiently apart from 1. The sensor cell also has a pair of sensor electrodes mounted on the reference chamber surface and the first detection chamber surface, respectively, and the electric signal is generated as a potential difference between the sensor electrodes.

The reference chamber may be vented to the atmosphere, with the reference gas being an atmospheric gas. Alternatively, the reference chamber may be isolated from the atmosphere, where the arrangement is such that the sensor is supplied with an electric current through the sensor electrodes, and oxygen is supplied from the detection chamber to the reference chamber to keep the reference gas excessively lean.

According to a second aspect of the present invention, there is provided an air-fuel ratio detecting device comprising a sensor, having a first detection surface which defines a detection chamber for introducing an exhaust gas atmosphere produced upon combustion of an air-fuel mixture through a diffusion hole, for generating an electric signal depending on the concentration of oxygen in a gas in the detection chamber, an oxygen ion conduction pump cell, having a second detection chamber surface defining the detection chamber, an exhaust gas surface for exposure to the exhaust gas atmosphere, and electrodes mounted respectively on the second detection chamber surface and the exhaust gas surface, for forcibly moving oxygen ions between the second detection chamber surface and the exhaust gas surface in response to an electric control signal applied between the electrodes and for generating an electromotive force depending on the difference between the concentration of oxygen in the gas in the detection chamber and the concentration of oxygen in the exhaust gas atmosphere, control means for applying the electric control signal between the electrodes in order to cause the gas in the detection chamber to indicate a nearly stoichiometric ratio in response to the electric signal from the sensor, first detecting means for producing an air-fuel ratio signal corresponding to the concentration of oxygen in the exhaust gas atmosphere based on the magnitude of the electric control signal, second detecting means for comparing a voltage between the electrodes and a threshold value close to a stoichiometric ratio, and for producing a output signal representing the result of the comparison, and threshold value setting means for variably setting the threshold value.

The threshold value setting means comprises means for establishing a plurality of threshold values depending on an operating condition of an engine with which the air-fuel ratio detecting device is associated.

The operating condition corresponds to a control parameter indicative of either the rotational speed of the engine or the load on the engine.

In the air-fuel ratio detecting device according to a first aspect of the present invention, the sensor cell and the pump cell are basically a $O_2$ sensors, which employ different reference gases. Therefore, the pump cell can also produce an electromotive force depending on an oxygen concentration difference. The pump cell generates such an electromotive force depending on the difference between the concentrations of oxygen in the gas in the detection chamber and the exhaust gas atmosphere. A potential difference between the terminals of the pump cell which is supplied with a pump current from the control means jumps by about 0.5 volt and thus discontinuously varies at a stoichiometric ratio as it is affected by the electromotive force.

Therefore, the stoichiometric ratio is detected by detecting the electromotive force depending on the oxygen concentration difference based on the potential difference between the terminals of the pump cell. Thus, the stoichiometric ratio can be calculated accurately with a good response without being adversely affected by errors and time lags of a control system connected to the sensor cell.

The air-fuel ratio detecting device according to the second aspect of the present invention is also capable of calculating a stoichiometric ratio without being affected by errors and time lags of the control system. In addition, since the threshold value can be increased or reduced by the threshold value setting means, an optimum threshold value depending on the type of catalyst used can be employed to effect fine adjustments of a corrected target stoichiometric ratio.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Like or corresponding parts are denoted by like or corresponding reference numerals throughout views.

Figure 1:
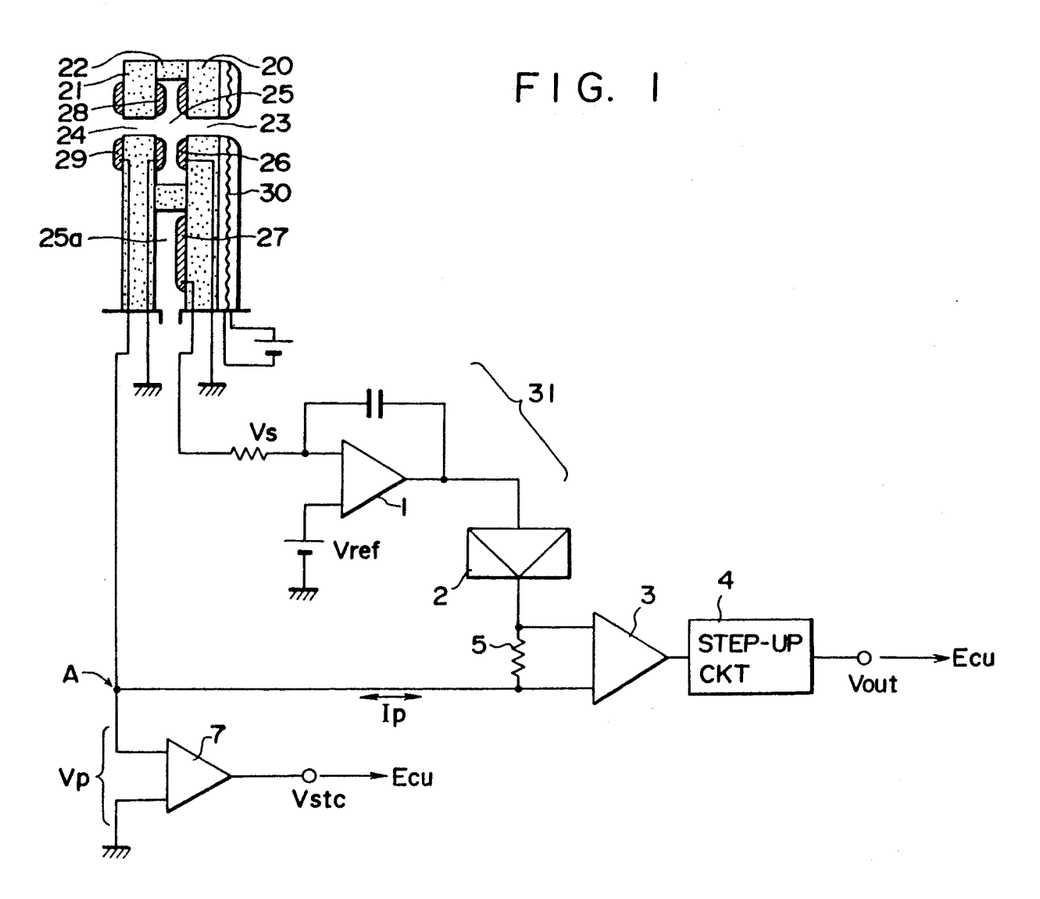
FIG. 1 is a schematic view, in a partial block form, of an air-fuel ratio detecting device according to an embodiment of the present invention.

FIG. 1 shows an air-fuel ratio detecting device according to an embodiment of the present invention. The air-fuel ratio detecting device shown in FIG. 1 includes components identical to some of the components of the conventional air-fuel ratio detecting device shown in FIG. 14. However, as described later on, the air-fuel ratio detecting device according to the present invention does not have a current inversion detector 6. However, the air-fuel ratio detecting device has a pump voltage detector 7.

As shown in FIG. 1, the air-fuel ratio detecting device includes a sensor cell 20 and a pump cell 21 which are coupled to each other through an insulation layer 22, and each of the cells is a stabilized zirconia device. The sensor cell 20 and the pump cell 21 have respective diffusion holes 23, 24 defined therein for passing therethrough exhaust gases while controlling the speed thereof. The insulation layer 22 has a detecting cavity 25 defined therein into which exhaust gases can be introduced through the diffusion holes 23, 24 by the sensor cell 20 and the pump cell 21. The detecting cavity 25 serves as an element for controlling the speed at which the exhaust gases are diffused. The insulation layer 22 also has a reference chamber 25a positioned below the detecting cavity 25 in a spaced-apart relation thereto, and the reference chamber 25a is defined between the sensor cell 20 and the pump cell 21. A reference gas such as atmospheric air is introduced into the reference chamber 25a through a communication hole (not shown).

The sensor cell 20 has porous electrodes 26, 27 of platinum, and the pump cell 21 has porous electrodes 28, 29 of platinum. The linear A/F sensor also has an electric heater 30 for heating itself to a temperature range, e.g., 800°±100° C., in which the sensor and pump cells 20, 21 can operate without fail.

The sensor cell 20 functions as an $O_2$ sensor for developing an electromotive force, depending on the oxygen concentration difference, between the electrodes 26, 27. The pump cell 21 serves to pump oxygen from a negative electrode to a positive electrode when an electric current (pump current Ip) is caused to flow between the electrodes 28, 29.

A controller 31 detects an electromotive force Vs developed by the sensor cell 20 through the electrodes 26, 27, and also controls the pump current Ip through a feedback loop to energize the pump cell 21 in order to keep an oxygen concentration corresponding to a stoichiometric ratio in the cavity 25 or the diffusion holes 23, 24. The controller 31 includes a comparator 1 and an integrator amplifier 2 with positive and negative power supplies. The comparator 1 compares the electromotive force Vs and a reference voltage Vref (of 0.4 volt, for example). The output signal from the comparator 1 is integrated by the integrator amplifier 2, whose integral output signal is applied through a resistor 5 between the electrodes 28, 29 of the pump cell 21. Based on the output signal from the integrator amplifier 2, the pump cell 21 moves oxygen ions so that the electromotive force Vs is equalized to the reference voltage Vref, i.e., an air-fuel ratio corresponding to the reference voltage is detected by the sensor cell 20.

The resistor 5 and a current detector 3 jointly serve as a first detecting device. More specifically, based on a voltage drop across the resistor 5, the current detector 3 indirectly detects the pump current Ip which is supplied to the pump cell 21 when the output signal from the integrator amplifier 2 is applied. The pump current Ip is then converted into an air-fuel ratio signal Vout in the range of from 0 to 5 volts by a step-up circuit 4 according to the equation (1) above.

The pump voltage detector 7, serving as a second detecting device, is supplied with a pump voltage Vp equal to a potential at a point A, i.e., between the electrodes 28, 29.

Figures 2A, 2B:
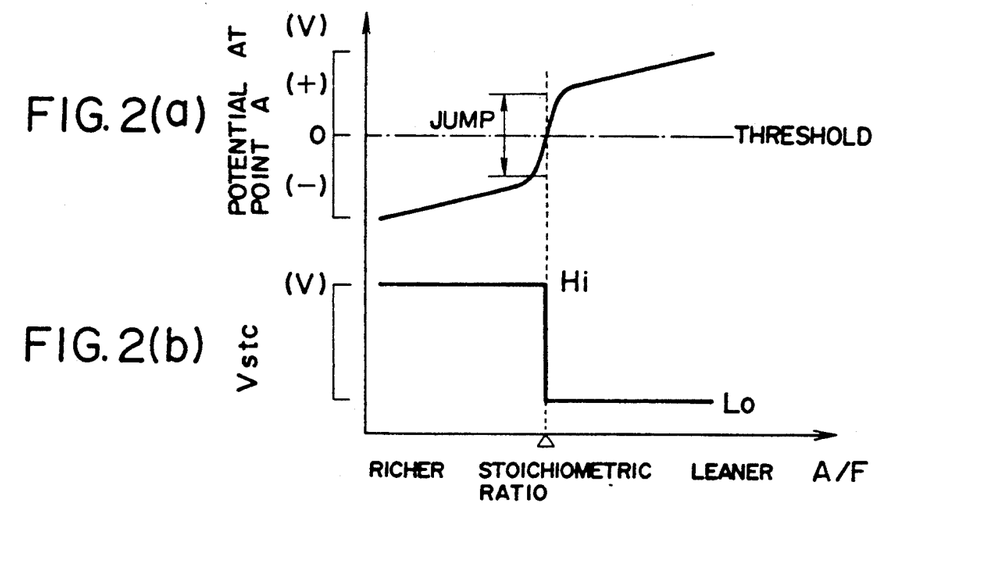
FIGS. 2(a) and 2(b) are diagrams showing signal waveforms illustrative of the operation of the air-fuel ratio detecting device shown in FIG. 1.

As shown in FIG. 2(a), the pump voltage Vp has a discontinuous region where its level jumps across a stoichiometric ratio. The pump voltage detector 7 is supplied with a suitable threshold value for detecting such a discontinuous region. Therefore, as shown in FIG. 2(b), the output signal from the pump voltage detector 7 switches between high and low levels across the stoichiometric ratio, i.e., between leaner and richer sides of the stoichiometric ratio. The output signal from the pump voltage detector 7 is referred to as a stoichiometric ratio signal Vstc.

The stoichiometric ratio signal Vstc may have a high level on the richer side and a low level on the leaner side, as shown, or vice versa.

Figure 3:
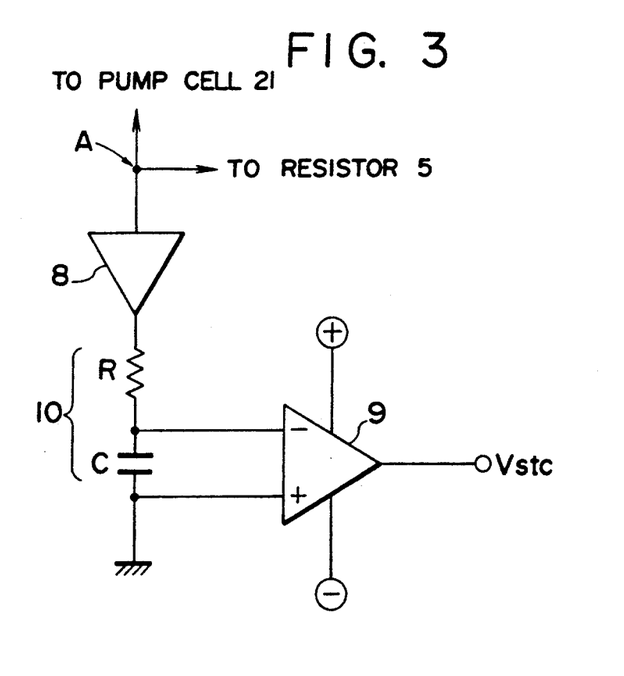
FIG. 3 is a block diagram of a second detecting device in the air-fuel ratio detecting device shown in FIG. 1.

FIG. 3 shows a specific arrangement of the second detecting device or the pump voltage detector 7. The pump voltage detector 7 includes a buffer amplifier 8, a CR filter 10, and an open-collector comparator 9.

The voltage at the point A in FIG. 3 is applied through the buffer amplifier 8 and the CR filter 10 to an inverting input terminal of the comparator 9. The CR filter 10 is provided to remove voltage surges or noise from the applied voltage whose level tends to switch quickly between the high and low levels due to ripples of the pump current Ip caused by exhaust gas pulsations. The comparator 9 has its noninverting input terminal grounded, i.e., has a threshold value of 0 volt for comparison with the voltage supplied from the CR filter 10. The comparator 9 produces at its output terminal the stoichiometric ratio signal Vstc.

Figures 4, 5A:
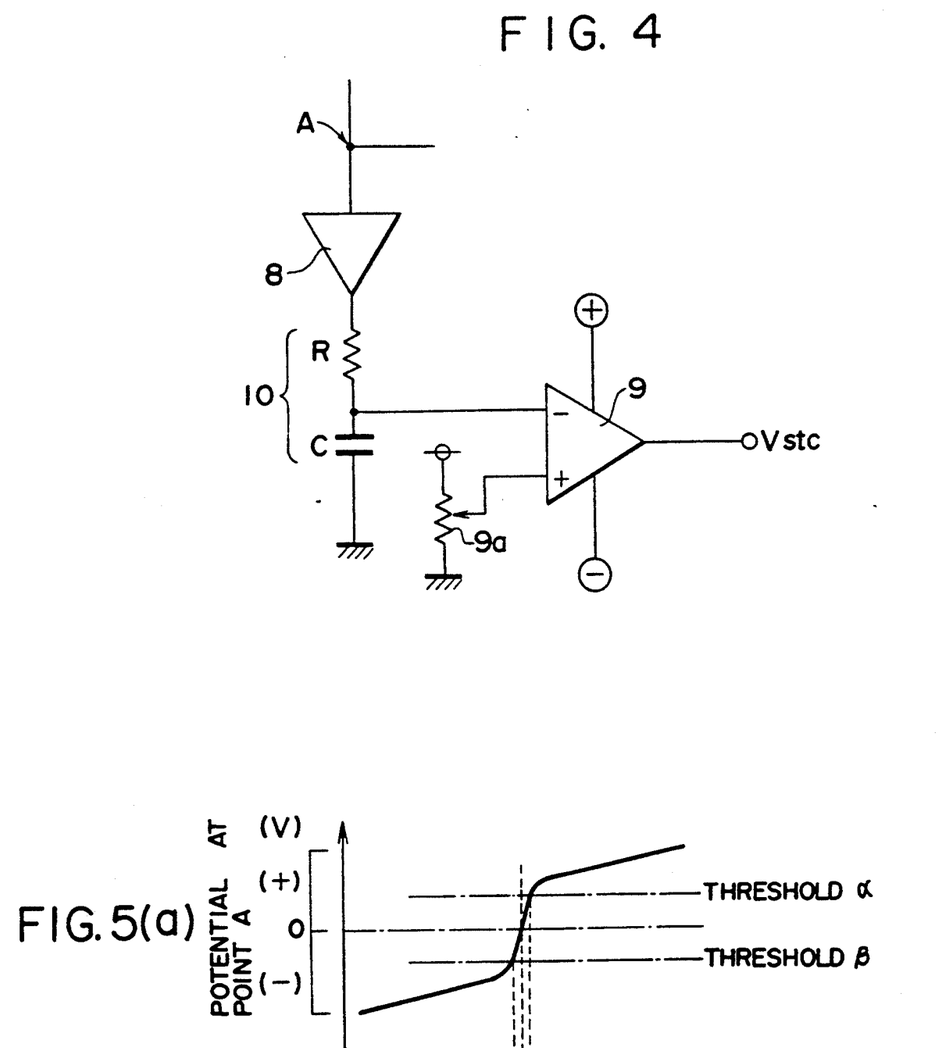
FIG. 4 is a block diagram of another second detecting device.
FIGS. 5(a) and 5(b) are diagrams showing signal waveforms illustrative of the operation of the second detecting device shown in FIG. 4.

FIG. 4 shows a specific arrangement of another pump voltage detector or second detecting device. The pump voltage detector shown in FIG. 4 differs from the pump voltage detector 7 shown in FIG. 3 in that a variable threshold value or voltage can be applied to the noninverting input terminal of the comparator 9.

More specifically, a variable voltage setting unit including a potentiometer 9a is employed as a threshold value setting device, and applies a voltage as a threshold value to the noninverting input terminal of the comparator 9. The voltage at the point A is applied through the buffer amplifier 8 and the CR filter 10 to the inverting input terminal of the comparator 9.

When the threshold value is shifted toward a positive side and set to a threshold value $\alpha$, as shown in FIG. 5(a), the stoichiometric ratio signal Vstc from the comparator 9 changes its level at a point on the leaner side of the stoichiometric ratio. When the threshold value is shifted toward a negative side and set to a threshold value $\beta$, as shown in FIG. 5(a), the stoichiometric ratio signal Vstc from the comparator 9 changes its level at a point on the richer side of the stoichiometric ratio. By thus shifting the threshold value to a positive or negative value, the point at which the stoichiometric ratio signal Vstc changes its level is slightly deviated from the stoichiometric ratio. This variable threshold value offers the following advantages: It is desirable to suitably select the point at which the stoichiometric ratio signal Vstc changes its level, depending on different proportions and quantities of exhaust gas components at the inlet of the three-way catalytic converter (e.g., different amounts of CO or NOx are emitted from different automobile types even if the air-fuel ratio remains the same), or different purifying efficiencies of three-way catalytic converters (e.g., different three-way catalytic converters have different absolute values of purifying efficiencies due to different capacities, for example, even if they have the same purifying characteristic tendency, as shown in FIG. 9).

When the target air-fuel ratio in the stoichiometric ratio control process is shifted to the richer side, more NOx can be purified. The threshold value thus selected is suitable for automobiles which emit a lower amount of CO and a large amount of NOx. When the target air-fuel ratio in the stoichiometric ratio control process is shifted to the leaner side, more CO and HC can be purified. The threshold value thus selected is suitable for automobiles which emit a small amount of NOx and a large amount of CO. Accordingly, the pump voltage detector shown in FIG. 4 can provide optimum exhaust gas purification characteristics for different automobile types.

Figure 5B:
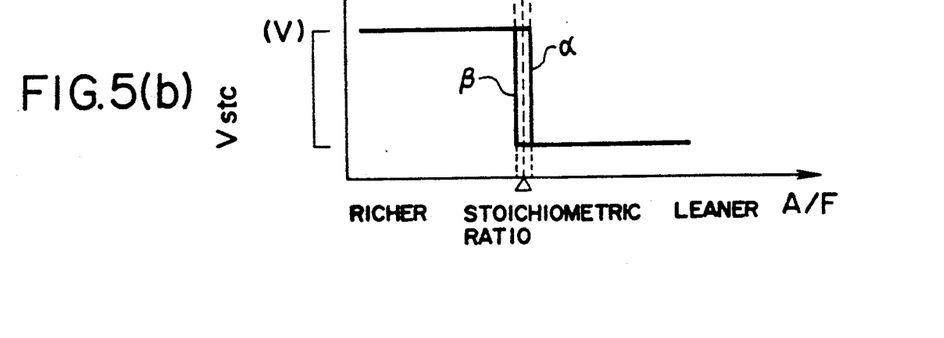

FIG. 5 shows a specific arrangement of still another pump voltage detector or second detecting device. As shown in FIG. 5, the voltage applied to the pump cell 21 is applied through the CR filter 10 and a resistor 12 to the inverting input terminal of an operational amplifier 11. The output signal from the operational amplifier 11 is also fed back to the inverting input terminal thereof. The operational amplifier 11 has a noninverting input terminal supplied with an upshifting voltage from a resistive voltage divider 14. Two series-connected diodes 15, 16 are connected in a reverse-biased manner between a power supply of a given voltage and ground. The junction between the diodes 15, 16 is connected to the output terminal of the operational amplifier 11 through a resistor 17. The diodes 15, 16 can slip the output signal from the operational amplifier 11 at a predetermined voltage.

Figures 7A, 7B:
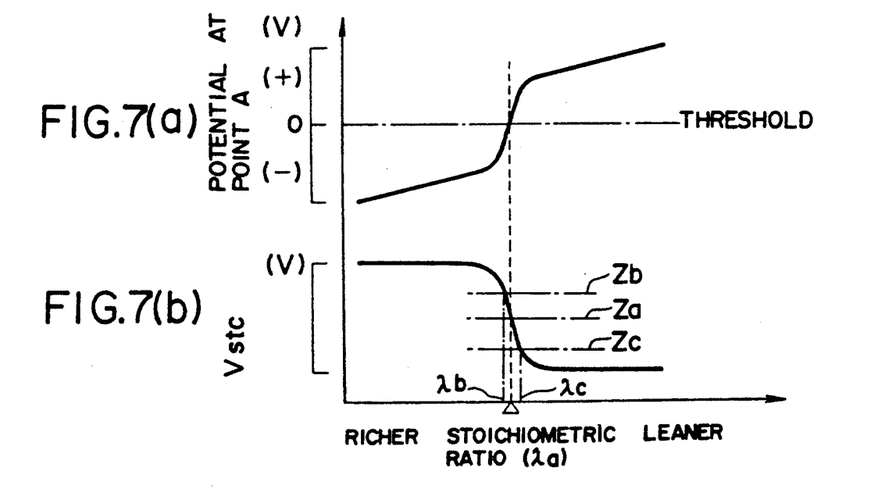
FIGS. 7(a) and 7(b) are diagrams showing signal waveforms illustrative of the operation of the second detecting device shown in FIG. 6.

FIG. 7(a) shows the potential at the point A, the potential varying its level discontinuously at the stoichiometric ratio. The stoichiometric ratio signal Vstc produced varies slightly and smoothly in the vicinity of the stoichiometric ratio as shown in FIG. 7(b), so that output signal characteristics similar to those of a so-called $\gamma$ sensor are produced as a result.

Different threshold values Za, Zb, Zc, for example, are established with respect to the stoichiometric ratio signal Vstc, as shown in FIG. 7(b). By using such different threshold values Za, Zb, Zc, corrected stoichiometric ratios $\lambda a$, $\lambda b$ (shifted to the richer side), and $\lambda c$ (shifted to the leaner side) are allowed to be detected as target air-fuel ratios from the stoichiometric ratio signal with the above output signal characteristics.

The threshold values Za, Zb, . . . (which are also collectively be referred to as Zi) are defined in a map shown in FIG. 10. The map shown in FIG. 10 contains a plurality of selective threshold values based on control parameters which include an engine rotational speed N and a volumetric efficiency Ev which is one form of engine load information. If the engine rotational speed N changes from one side to the other of a level a or from one side to the other of a level b, then the threshold value Zi is shifted from Z0 (Z3) to Z1 (Z4) or from Z1 (Z4) to Z0 (Z3), or from Z1 (Z4) to Z2 (Z5) or from Z2 (Z5) to Z1 (Z4). If the volumetric efficiency Ev changes from one side to the other of a level c, then the threshold value Zi is shifted from Z0 (Z1, Z2) to Z3 (Z4, Z5) or from Z3 (Z4, Z5) to Z0 (Z1, Z2).

The threshold values Zi are selected according to automobile type, catalytic characteristics, and other parameters.

Figure 10:
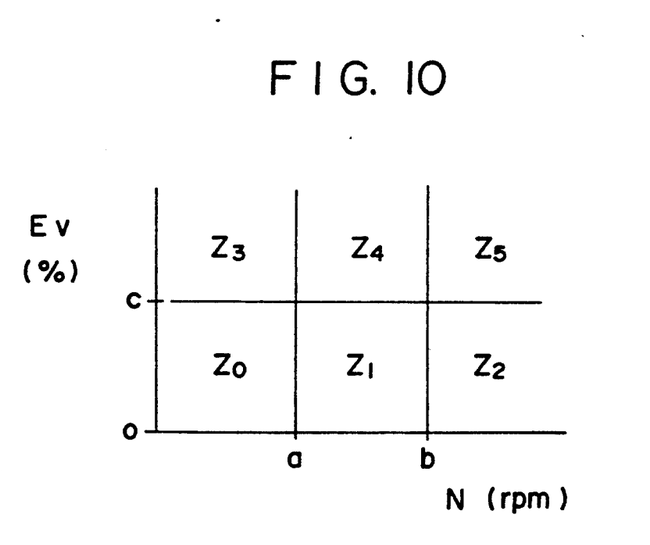
FIG. 10 is a diagram showing a map of threshold values.

The threshold value for the stoichiometric ratio signal Vstc is set by a threshold value setting device which is implemented by a control unit indicated as ECU in FIG. 1. The control unit ECU is mainly composed of a microcomputer, and reads information from the stoichiometric ratio signal Vstc for producing a control signal from time to time. The control unit ECU stores, and operates according to, programs of a routine for setting a Vstc threshold value as shown in FIGS. 11(a), 11(b), and a routine for calculating a fuel injection rate as shown in FIG. 12, and the map of threshold values or levels Zi as shown in FIG. 10.

A fuel feedback control process using the stoichiometric ratio signal Vstc and the air-fuel ratio signal Vout will now be described below with reference to FIGS. 11(a), 11(b), and 12.

Figure 11A:
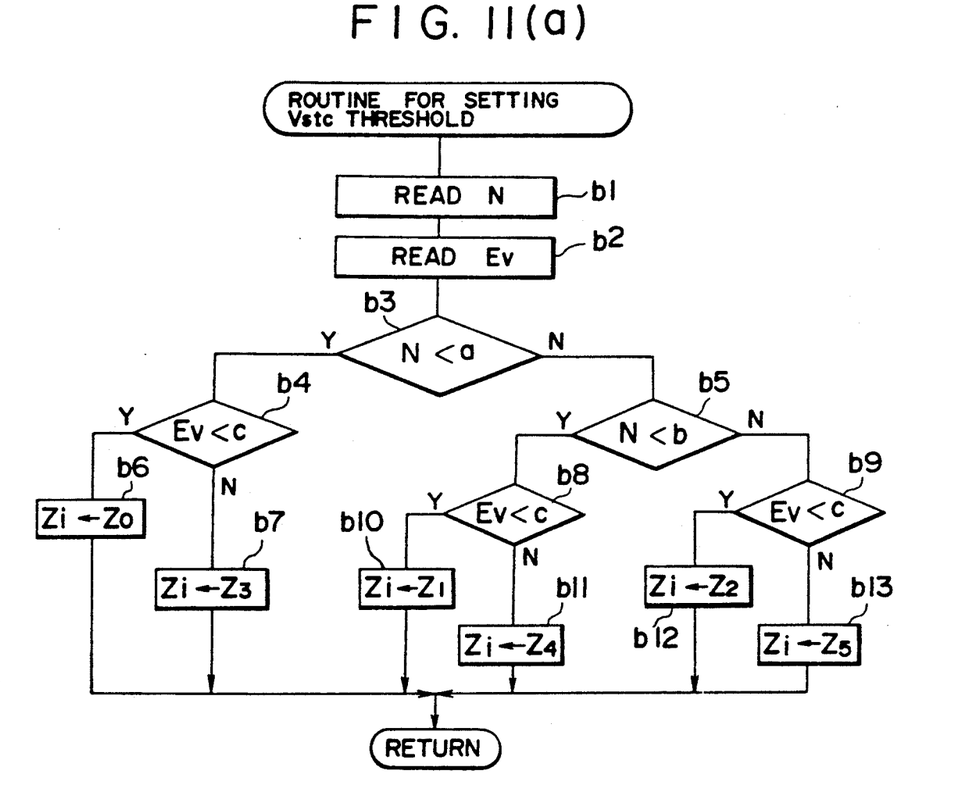
FIG. 11(a) is a flowchart of a routine for setting a Vstc threshold value.
Figure 11B:
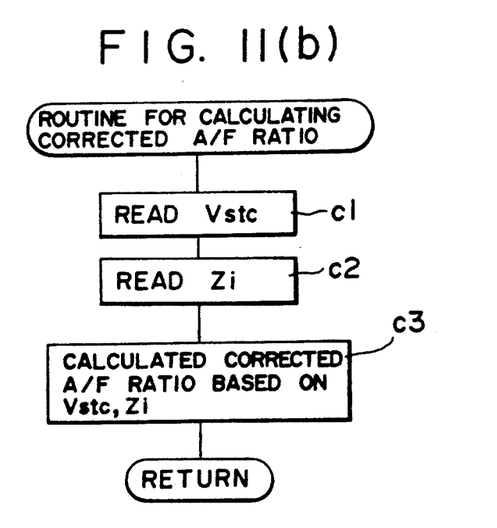
FIG. 11(b) is a flowchart of a routine for calculating a corrected air-fuel ratio.
Figure 12:
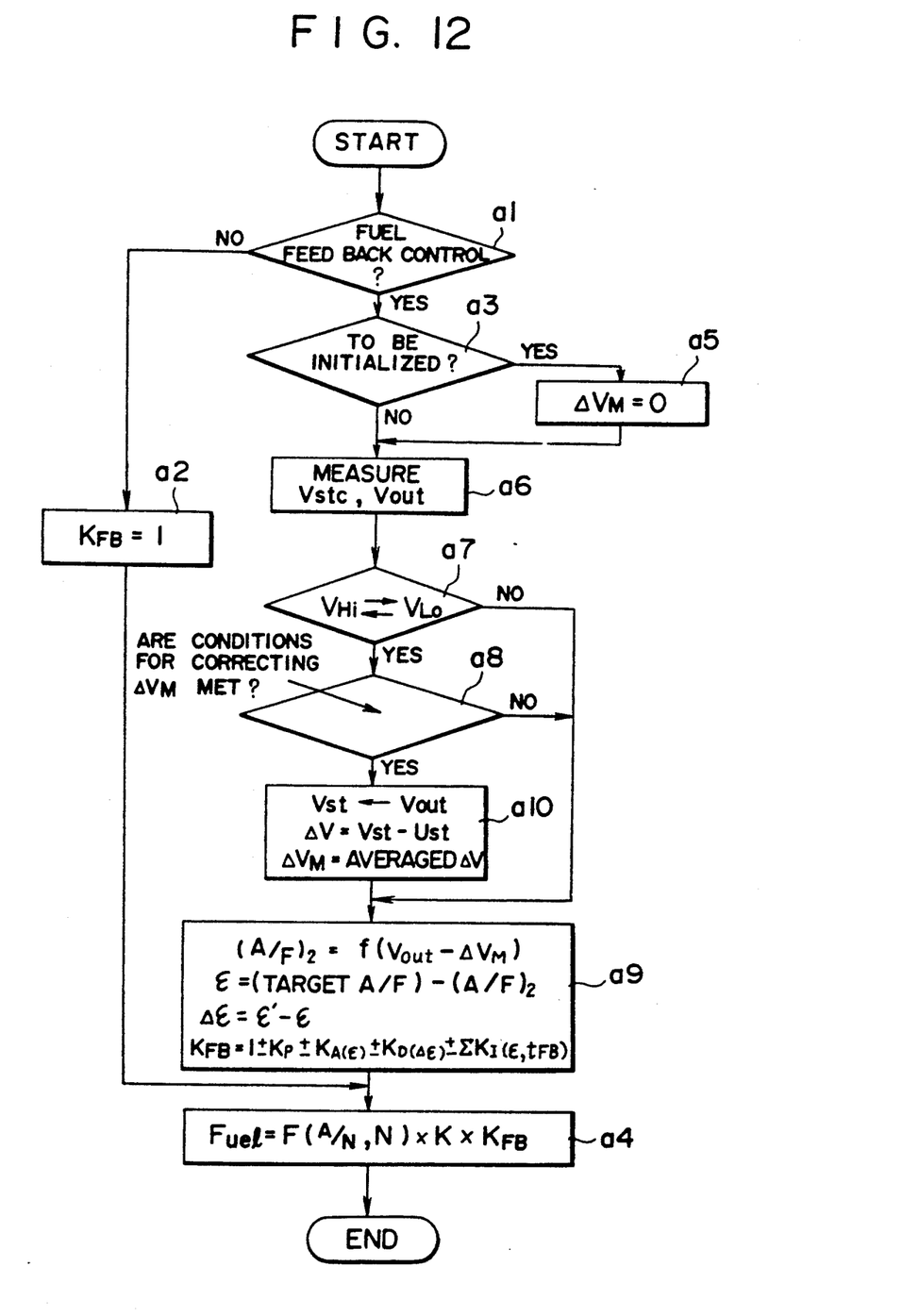
FIG. 12 is a flowchart of a routine for calculating a fuel ejection rate.

The routine for setting a Vstc threshold value shown in FIGS. 11(a) and 11(b) is executed under a certain stoichiometric ratio feedback condition in a main control routine (not shown).

In the routine for setting a Vstc threshold value, an engine rotational speed N and a volumetric efficiency Ev (determined from an amount of air drawn into an engine cylinder per stroke) are read in respective steps b1, b2. Then, a step b3 determines whether the engine rotational speed N is lower than the level a or not. If the engine rotational speed N is lower than the level a, then control goes to a step b4 which determines whether the volumetric efficiency Ev is smaller than the level c or not. If the volumetric efficiency Ev is equal to or larger than the level c in the step b4, then the threshold value Z3 is read into a threshold address Zi in a memory in a step b7. If the volumetric efficiency Ev is smaller than the level c in the step b4, then the threshold value Z0 is read into the threshold address Zi in a step b6. Thereafter, control returns from the Vstc threshold value setting routine back to the main routine.

If the engine rotational speed N is equal to or higher than the level a in the step b3, then control goes to a step b5 which determines whether the engine rotational speed N is lower than the level b or not. If the engine rotational speed N is lower than the level b, i.e., in the range of a<N<b, then control goes to a step b8. If the engine rotational speed N is higher than the level b, then control goes to a step b9.

The step b8 determines whether the volumetric efficiency Ev is smaller than the level c or not. If the volumetric efficiency Ev is smaller than the level c in the step b8, then the threshold value Z1 is read into the threshold address Zi in a step b10. If the volumetric efficiency Ev is equal to or larger than the level c in the step b8, then the threshold value Z4 is read into the threshold address Zi in a step b11.

The step b9 determines whether the volumetric efficiency Ev is smaller than the level c or not. If the volumetric efficiency Ev is smaller than the level c in the step b8, then the threshold value Z2 is read into the threshold address Zi in a step b12. If the volumetric efficiency Ev is equal to or larger than the level c in the step b9, then the threshold value Z5 is read into the threshold address Zi in a step b13.

Control returns from the steps b10, b11, b12, b13 back to the main routine.

In the routine for calculating a corrected stoichiometric ratio (corrected A/F ratio) shown in FIG. 11(b), the stoichiometric ratio signal Vstc and the threshold value Zi are read in respective steps c1, c2. Then, a step c3 calculates a corrected stoichiometric ratio based on the stoichiometric ratio signal Vstc and the threshold value Zi. Thereafter, control goes back to the main routine.

The routine for calculating a fuel injection rate shown in FIG. 12 is basically divided into three step groups. In the first step group, the timing at which a stoichiometric ratio is reached is determined on the basis of the stoichiometric ratio signal Vstc. The second step group determines the difference or error $\Delta V$ ($=Vst-Ust$) between an air-fuel ratio signal Vst and a predetermined stoichiometric ratio signal Ust (including signals corresponding to $\lambda b$, $\lambda c$, which are shifted to the richer and leaner sides). The subsequent third step group corrects the air-fuel ratio signal Vout with the error $\Delta V$, thus obtaining an actual air-fuel ratio. A fuel injection valve of an engine which incorporates the air-fuel ratio detecting device according to the present invention is then opened with a predetermined timing for a suitable period of time according to the above routine.

More specifically, when the program for the routine is started, a step a1 determines whether a condition for effecting a fuel feedback control process is met or not, based on an input signal from a known detecting device. If the condition is not met, then control goes to a step a2, and if the condition is met, then control goes to a step a3.

In the step a2, a fuel injection rate corrective coefficient KFB is set to "1". Then, control proceeds to a step a4 in which a fuel injection rate Fuel is calculated. At this time, a basic fuel injection rate F(A/F,N) is calculated from an air inlet rate A/F per unit engine rotational speed, produced by an interrupt routine (not shown), and the engine rotational speed N. Then, the calculated basic fuel injection rate F(A/F,N) is multiplied by the corrective coefficient KFB and another corrective coefficient K depending on a parameter such as the atmospheric pressure, thus obtaining the fuel injection rate Fuel. Thereafter, control returns to the main routine. The air inlet rate A/F may be replaced with an intake air pressure, a throttle opening, or the like.

If the condition is met in the step a1, then control goes to a step a3 which determines whether an average value $\Delta VM$ of errors $\Delta V$ is to be cleared or initialized. If the average value $\Delta VM$ is to be cleared, then it is cleared in a step a5, which is then followed by a step a6.

The step a6 reads the corrected stoichiometric ratio signal Vstc and the air-fuel ratio signal Vout.

A step a7 compares the read value of Vstc with the value in the previous cycle, and determines whether they differ form each other, i.e., the stoichiometric ratio signal Vstc has changed from the high level VHI to the low level VLO or from the low level VLO to the high level VHI. If the stoichiometric ratio signal Vstc has changed in level because the present air-fuel ratio has reached the stoichiometric ratio, then control goes to a step a8, and if the stoichiometric ratio signal Vstc has not changed, control goes to a step a9.

The step a8 determines whether conditions for correcting the average value ΔVM are satisfied (e.g., if the accelerator or throttle opening has changed by a value less than or equal to a reference, if the target air-fuel ratio has been modified immediately before, etc.). If the conditions are met, then control goes to a step a10, and if the conditions are not met, control goes to a step a9.

In the step a10, the air-fuel ratio signal Vout is read, and substituted in an actual value Vst at the time the air-fuel ratio has reached the stoichiometric ratio. Then, a difference ΔV is calculated between the actual value Vst and a predetermined stoichiometric ratio Ust, and an average value ΔVM of the present and previous differences or errors ΔV in order to eliminate disturbances.

The step a9 corrects the air-fuel ratio signal Vout at the time with the average value ΔVM, for thereby producing an air-fuel ratio indicated by $(A/F)z = f$-(Vout−ΔVM), for example, which is a function of the difference between the air-fuel ratio signal Vout and the average value ΔVM.

Then, a difference or error $\epsilon$ is calculated between the target air-fuel ratio A/F and the actual air-fuel ratio (A/F)z, and a difference $\Delta\epsilon$ is calculated between the presently calculated error $\epsilon$ and the previously calculated error $\epsilon'$. Finally in the step a9, a corrective coefficient KFB is calculated for the control of a fuel injection rate based on the air-fuel ratio. The corrective coefficient KFB is determined as the sum of a proportional term $KA(\epsilon)$ depending on the level of the error $\epsilon$, an offset Kp for the prevention of a response delay owing to the three-way catalytic converter, a differential term $KD(\Delta\epsilon)$, an integral term $\Sigma KI(\epsilon, tFB)$, and 1.

Then, control proceeds to the step a4 in which the fuel injection rate Fuel is calculated as described above. Thereafter, control goes back to the main routine.

Figure 8:
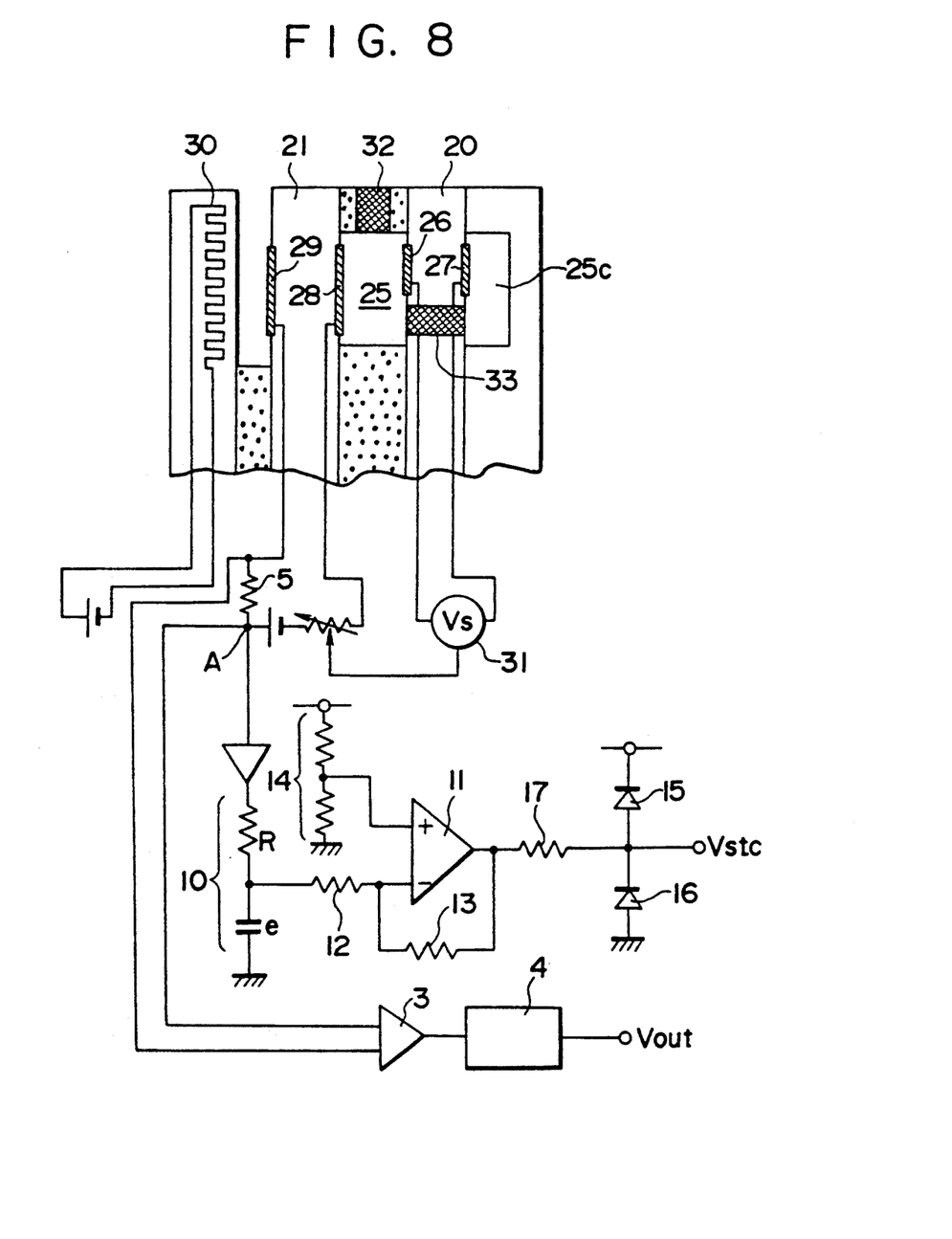
FIG. 8 is a schematic view, in a partial block form, of an air-fuel ratio detecting device according to another embodiment of the present invention.

FIG. 8 shows an air-fuel ratio detecting device according to another embodiment of the present invention. As shown in FIG. 8, the electrode 26 of the sensor cell 20 is disposed in confronting relation to the cavity 25, and the other electrode 27 to a reference chamber 25c which is defined on the other side of the sensor cell 20 remotely from the reference chamber 25. An electromotive force Vs is developed due to the potential difference between the electrodes 26, 27 depending on the difference between oxygen concentrations in the cavity 25 and the reference chamber 25c. The electrodes 26, 27 are supplied with a self-drawn current (not shown). The reference chamber 25c is kept in an excessively lean condition, i.e., with the air excess ratio therein being sufficiently apart from 1, and the gas contained in the reference chamber 25c serves as a reference gas. Denoted at 32, 33 are diffusion passages.

Figure 6:
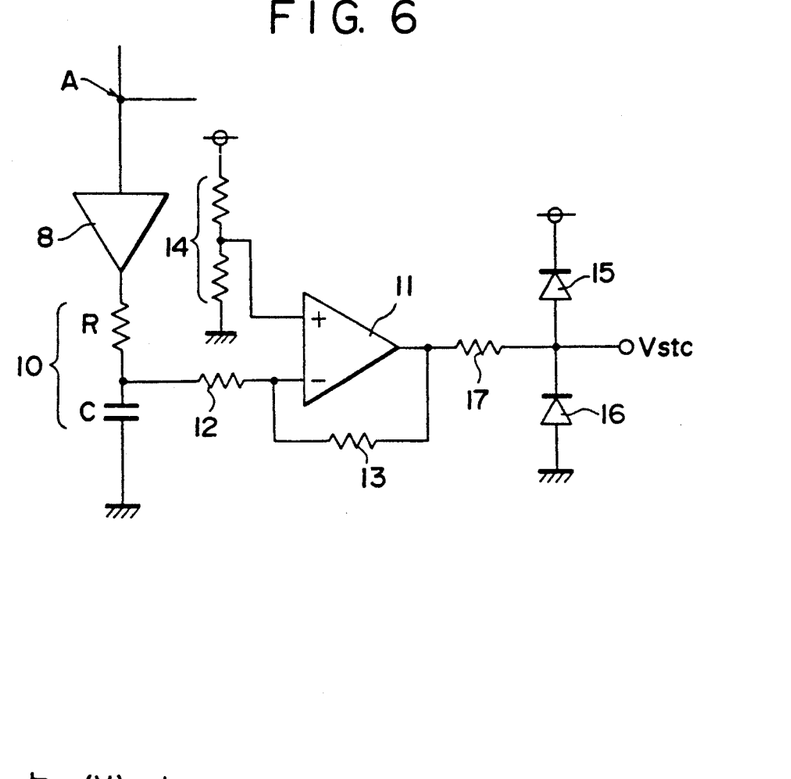
FIG. 6 is a block diagram of still another second detecting device.

The electrode 28 of the pump cell 21 is disposed in confronting relation to the cavity 25. The pump cell 21 is supplied, through the electrodes 28, 29, with a pump current Ip based on the sum of the first electromotive force Vs which is supplied through a variable resistor 6 from the controller 31 and a second electromotive force Va. The current detecting resistor 5, the current detector 3, and the step-up circuit 4 jointly serve to detect the air-fuel ratio signal Vout. Based on the pump current Ip at the point A, the stoichiometric ratio signal Vstc is detected by the same pump voltage detector as shown in FIG. 6. If the stoichiometric ratio signal Vstc is used as a corrected stoichiometric ratio signal which is processed based on the threshold value Zi, as shown in FIG. 12, then optimum exhaust gas purification characteristics can be obtained.

Other than the stoichiometric ratio feedback control of fuel based on the signals Vout, Vstc, it is also possible to effect a stoichiometric ratio feedback control process using only the stoichiometric ratio signal Vstc according to the same logic and procedure as with the conventional $O_2$ sensor. the air-fuel ratio detecting device according to the present invention can therefore be used in either one of these control processes.

As described above, an electromotive force developed depending on an oxygen concentration difference by the pump cell is directly or indirectly detected for the determination of a stoichiometric ratio. Therefore, the accuracy and response with which a stoichiometric ratio is detected are improved without being adversely affected by errors of the control system.

Since the threshold value for the stoichiometric ratio signal can be varied, fine adjustments can be achieved to obtain a corrected target stoichiometric ratio. The stoichiometric ratio signal which is slightly shifted to the richer or leaner side is effective to obtain optimum exhaust gas purification characteristics.

Although certain preferred embodiments have been shown and described, it should be understood that many changes and modifications may be made therein without departing from the scope of the appended claims.

What is claimed is:

1. An air-fuel ratio detecting device comprising:
   a sensor, having a first detection surface, which defines a detection chamber for introducing an exhaust gas atmosphere produced upon combustion of an air-fuel mixture through a diffusion hole, for generating an electric signal depending on the concentration of oxygen in a gas in said detection chamber;
   an oxygen ion condition pump cell, having a second detection chamber surface, which defines said detection chamber, an exhaust gas surface for exposure to the exhaust gas atmosphere, and electrodes mounted respectively on said second detection chamber surface and said exhaust gas surface, for forcibly moving oxygen ions between said second detection chamber surface and said exhaust gas surface in response to an electric control signal applied between said electrodes and for generating an electromotive force depending on the difference between the concentration of oxygen in the gas in said detection chamber and the concentration of oxygen in the exhaust gas atmosphere;
   control means for applying said electric control signal between said electrodes in order to cause the gas in said detection chamber to indicate a nearly stoichiometric ratio in response to the electric signal from said sensor;
   first detecting means for producing an air-fuel ratio signal corresponding to the concentration of oxygen in the exhaust gas atmosphere based on the magnitude of said electric control signal; and
   second detecting means for detecting a voltage between said electrodes and producing a detected output signal when the exhaust gas atmosphere indicates a stoichiometric ratio.

2. An air-fuel ratio detecting device according to claim 1, wherein each of said electrodes is porous and made of platinum.

3. An air-fuel ratio detecting device according to claim 1, wherein said pump cell is made of zirconia.

4. An air-fuel radio detecting device according to claim 1, further including an electric heater for heating at least said pump cell.

5. An air-fuel ratio detecting device according to claim 1, wherein said sensor comprises an oxygen ion conduction sensor cell, said oxygen ion conduction sensor cell having a reference chamber surface which defines a reference chamber for being filled with a reference gas having an air excess ratio which is greater than 1 or less than 1 by a predetermined value, said oxygen ion conduction sensor cell also having a pair of sensor electrodes mounted on said reference chamber surface and said first detection chamber surface, respectively, said electric signal being generated as a potential difference between said sensor electrodes.

6. An air-fuel ratio detecting device according to claim 5, wherein reference chamber is vented to the atmosphere, said reference gas being an atmospheric gas.

7. An air-fuel ratio detection device according to claim 5, wherein said reference chamber is isolated from the atmosphere so that said sensor is supplied with an electric current through said sensor electrodes, and oxygen is supplied from said detection chamber to said reference chamber to keep said reference gas excessively lean.

8. An air-fuel ratio detecting device comprising:
a sensor, having a first detection surface, which defines a detection chamber for introducing an exhaust gas atmosphere produced upon combustion of an air-fuel mixture through a diffusion hole, for generating an electric signal depending on the concentration of oxygen in a gas in said detection chamber;
an oxygen ion conduction pump cell, having a second detection chamber surface, which defines said detection chamber, an exhaust gas surface for exposure to the exhaust gas atmosphere, and electrodes mounted respectively on said second detection chamber surface and said exhaust gas surface, for forcibly moving oxygen ions between said second detection chamber surface and said exhaust gas surface in response to an electric control signal applied between said electrodes and for generating an electromotive force depending on the difference between the concentration of oxygen in the gas in said detection chamber and the concentration of oxygen in the exhaust gas atmosphere;
control means for applying said electric control signal between said electrodes in order to cause the gas in said detection chamber to indicate a nearly stoichiometric ratio in response to the electric signal from said sensor;
first detecting means for producing an air-fuel ratio signal corresponding to the concentration of oxygen in the exhaust gas atmosphere based on the magnitude of said electric control signal;
second detecting means for comparing a voltage between said electrodes and a threshold value close to a stoichiometric ratio, and for producing an output signal representing the result of comparison; and
threshold value setting means for variably setting said threshold value.

9. An air-fuel ratio detecting device according to claim 8, wherein each of said electrodes is porous and made of platinum.

10. An air-fuel ratio detecting device according to claim 8, wherein said pump cell is made of zirconia.

11. An air-fuel ratio detecting device according to claim 8, further including an electric heater for heating at least said pump cell.

12. An air-fuel ratio detecting device according to claim 8, wherein said sensor comprises an oxygen ion conduction sensor cell, said oxygen ion conduction sensor cell having a reference chamber surface which defines a reference chamber for being filled with a reference gas having an air excess ratio which is greater than 1 or less than 1 by a predetermined value, said oxygen ion conduction sensor cell also having a pair of sensor electrodes mounted on said reference chamber surface and said first detection chamber surface, respectively, said electric signal being generated as a potential difference between said sensor electrodes.

13. An air-fuel ratio detecting device according to claim 12, wherein reference chamber is vented to the atmosphere, said reference gas being an atmospheric gas.

14. An air-fuel ratio detecting device according to claim 12, wherein said reference chamber is isolated from the atmosphere so that said sensor is supplied with an electric current through said sensor electrodes, and oxygen is supplied from said detection chamber to said reference chamber to keep said reference gas excessively lean.

15. An air-fuel ratio detecting device according to claim 8, wherein said threshold value setting means comprises means for establishing a plurality of threshold values depending on an operating condition of an engine associated with the air-fuel ratio detecting device.

16. An air-fuel ratio detecting device according to claim 15, wherein said operating condition corresponds to a control parameter indicative of either the rotational speed of the engine or the load on the engine.

17. A method for detecting an air-fuel ratio, comprising the steps of:
(a) generating an electric signal by a sensor having a first detection surface, which defines a detection chamber for introducing an exhaust gas atmosphere produced upon combustion of an air-fuel mixture through a diffusion hole, depending on the concentration of oxygen in a gas in said detection chamber;
(b) forcibly moving oxygen ions by an oxygen ion conduction pump cell having a second detection surface, which defines said detection chamber, an exhaust gas surface for exposure to the exhaust gas atmosphere and electrodes mounted respectively on said second detection chamber surface and said exhaust gas surface, between said second detection chamber surface and said exhaust gas surface in response to an electric control signal applied between said electrodes;
(c) generating an electromotive force depending on the difference between the concentration of oxygen in the gas in said detection chamber and the concentration of oxygen in the exhaust gas atmosphere;
(d) applying said electric control signal between said electrodes in order to cause the gas in said detection chamber to indicate a nearly stoichiometric ratio in response to the electric signal generated at said step (a);
(e) producing an air-fuel ratio signal corresponding to the concentration of oxygen in the exhaust gas atmosphere based on the magnitude of said electric control signal;
(f) detecting a voltage between said electrodes; and
(g) producing a detected output signal when the exhaust gas atmosphere indicates a stoichiometric ratio.

18. A method for detecting an air-fuel ratio, comprising the steps of:
(a) generating an electric signal by a sensor having a first detection surface, which defines a detection chamber for introducing an exhaust gas atmosphere produced upon combustion of an air-fuel mixture through a diffusion hole, depending on the concentration of oxygen in a gas in said detection chamber;
(b) forcibly moving oxygen ions by an oxygen ion conduction pump cell having a second detection surface, which defines said detection chamber, an exhaust gas surface for exposure to the exhaust gas atmosphere and electrodes mounted respectively on said second detection chamber surface and said exhaust gas surface, between said second detection chamber surface and said exhaust gas surface in response to an electric control signal applied between said electrodes;
(c) generating an electromotive force depending on the difference between the concentration of oxygen in the gas in said detection chamber and the concentration of oxygen in the exhaust gas atmosphere;
(d) applying said electric control signal between said electrodes in order to cause the gas in said detection chamber to indicate a nearly stoichiometric ratio in response to the electric signal generated at said step (a);
(e) producing an air-fuel ratio signal corresponding to the concentration of oxygen in the exhaust gas atmosphere based on the magnitude of said electric control signal;
(f) comparing a voltage between said electrodes and a threshold value close to a stoichiometric ratio;
(g) producing an output signal representing the result of the comparison at said step (f); and
(h) variably setting said threshold value.

* * * * *